United States Patent

Röper et al.

Patent Number: 5,879,373
Date of Patent: *Mar. 9, 1999

[54] SYSTEM AND METHOD FOR THE DETERMINATION OF TISSUE PROPERTIES

[75] Inventors: Josef Röper, Neuhofen; Dirk Böcker, Heidelberg, both of Germany

[73] Assignee: Boehringer Mannheim GmbH, Mannheim, Germany

[*] Notice: This patent issued on a continued prosecution application filed under 37 CFR 1.53(d), and is subject to the twenty year patent term provisions of 35 U.S.C. 154(a)(2).

[21] Appl. No.: 577,940

[22] Filed: Dec. 22, 1995

[30] Foreign Application Priority Data

Dec. 24, 1994 [DE] Germany ............................ 44 46 721.4
Jun. 22, 1995 [DE] Germany ............................ 195 22 706.9

[51] Int. Cl.[6] ........................................ A61B 5/00
[52] U.S. Cl. ..................... 606/344; 606/310; 606/322
[58] Field of Search ..................... 128/633, 664–667, 128/640, 641; 600/310, 314–316, 322–324, 326, 328, 340, 344, 473, 476, 386, 391

[56] References Cited

U.S. PATENT DOCUMENTS

| 4,274,418 | 6/1981 | Vesterager et al. |
|---|---|---|
| 4,830,014 | 5/1989 | Goodman et al. |
| 4,899,753 | 2/1990 | Inoue et al. ............................ 128/640 |
| 5,054,488 | 10/1991 | Muz. |
| 5,224,478 | 7/1993 | Sakai et al. ............................ 128/633 |

FOREIGN PATENT DOCUMENTS

| 0 573 137A2 | 12/1993 | European Pat. Off. |
|---|---|---|
| 34 40 401A1 | 5/1986 | Germany. |
| 6-152611 | of 1989 | Japan. |
| 4-111344 | of 1992 | Japan. |
| WO94/10901 | 5/1994 | WIPO. |

OTHER PUBLICATIONS

"Method for the Fixation of Optrodes in Near–Infa–red Spectrophotometry", Liem et al, Medical & Biological Engineering & Computing, Jan. 1992, pp. 120–121.

*Primary Examiner*—Michael Peffley
*Assistant Examiner*—Bryan K. Yarnell
*Attorney, Agent, or Firm*—Nikaido Marmelstein Murray & Oram LLP

[57] ABSTRACT

System for determining the properties of tissue parts of a living organism, comprising an optoelectronic measuring device (10) and an attachment device (20) which is opaque to light and surrounds a measuring window (28) through which determinations are carried out. The device (20) has one or several components (26) for reproducibly attaching the measuring device (10) in a direction toward a first surface of the tissue. Other subject matters of the invention are an attachment device (20) and a method for determining the properties of tissue parts with the aid of the claimed system.

24 Claims, 3 Drawing Sheets

5,879,373

SYSTEM AND METHOD FOR THE DETERMINATION OF TISSUE PROPERTIES

BACKGROUND OF THE INVENTION

1. Field of the Invention

Subject matter of the invention is a system for determining the properties of tissue parts of a living organism, a device for attaching an optoelectronic measuring device to the surface of the tissue, and a method for the non-invasive determination of the properties of tissue parts.

To date, the majority of determinations of properties of living organisms is carried out in the form of invasive methods. The structure of tissue is characterized, for example, with the aid of surgical methods. When an analyte is to be determined in body fluids, a certain amount of body fluid was obtained from the tissue, i.e. the human body, by obtaining blood from the veins, for example. These invasive methods lead to tissue damage, particularly when several determinations are carried out successively. It is for this reason that methods have then developed recently where the properties of tissue of the living organism can be determined even without withdrawing body fluids or surgical intervention.

2. Description of the Related Art

WO 94/10901 describes a method and device for analyzing glucose in a biological matrix which utilizes the multiple scattering of light by tissue. This patent application discloses that a measuring head is attached to a suitable site of the body weight the aid of an adhesive tape. In order to keep away foreign light sources, the measuring head is provided with a skin contact part whose diameter is considerably larger than the one of the measuring opening used. The ring is made of a non-transparent material and tightly urges against the skin.

U.S. Pat. No. 5,226,417 describes a device where a light beam is sent through a finger. The device is equipped with light-emitting diodes and photodetectors that are flexibly connected to one another so as to be arranged on opposite sides of the finger. The device also has wings to shield off light from the environment when the device is attached to the finger.

Moreover, the device described is provided with an adhesive tape to attach the light source and the photodetector to the skin. Object of the adhesive is to increase the resistance against undesired removal of the device.

U.S. Pat. No. 4,928,691 also describes a flexible device which comprises a photosensor and a light source. These elements are mounted on to a flexible material which, in turn, can be attached to various sites on the body. This is accomplished with the aid of an adhesive strip.

U.S. Pat. No. 5,267,563 describes a pulsoximeter whose sensors are attached to the skin with the aid of an adhesive plaster. The plaster contains substances to stimulate the blood flow. Once the drug has entered the skin, a measurement is carried out. When the measurement is completed the instrument is removed from the skin.

EP-A-0 573 137 describes a pulsoximeter where the sensors are attached to the skin with the aid of an adhesive strip which contains substances that stimulate the blood flow. In order to shield off light from the environment, the photodetector has a wall that reaches through the adhesive strip on to the skin. This device was designed for disposable use as are the other above mentioned devices.

U.S. Pat. No. 4,685,464 describes an element for attaching a sensor for the non-invasive measurement of blood components. The sensor can be attached to a finger.

EP-A-0 572 684 describes a sensor for monitoring life signs, especially saturation with oxygen. Said sensor can be attached to various sites of the skin. To do this, the described system has transmitter element as well as a receiver element which have been designed for multiple use. Moreover, the system has a housing to contain the above listed elements and connections for attachment of the above-mentioned elements.

In the devices and methods described in the above mentioned prior art, accuracy of positioning is irrelevant as a pulsoximetry application depends on the pulse signal rather than the site of the application.

U.S. Pat. No. 4,798,955 describes means for use of a non-invasive measuring device for several subject. It describes a flexible band which is placed around the upper arm of the subjects. The band has an element for individually adjusting the position of the band and, hence, of a measuring window. Experience has shown, however, that the reproducibility of the individual measurements is not satisfactory.

SUMMARY OF THE INVENTION

It was an object of the present invention to eliminate the drawbacks of the prior art either completely or at least partially.

It was a particular object of the invention to provide a system suitable for determining tissue properties which can also be used in long-term use.

This object is accomplished in that a measuring device is attached to an exactly defined position on the tissue surface.

Subject matter of the invention is, hence, a system for determining the properties of tissue parts of a living organism comprising an optoelectronic measuring device (10),
a device (20) that is opaque to light and surrounds a measuring window (28) through which the determination is carried out, the device has at least one component (26) to attach the measuring device (10) in a reproducible manner such that it is directed toward a first surface of the tissue.

Moreover, subject matters of the invention are a device for attaching an optoelectronic measuring device onto the surface of a tissue of a living organism and a method for determining properties of tissue parts of a living organism.

The subject matter of the present invention is particularly suitable for non-invasive determinations. Non-invasive determinations as understood in the invention are those methods where materials that are foreign to the body do not enter the surface of the tissue. The subject matters of the invention are particularly suitable for long-term use without negatively affecting the test subjects' well-being.

The system of the invention comprises an optoelectronic measuring device in which the actual measurements are carried out. Principally, it is possible to use any optoelectronic measuring device known in prior art in the system of the invention if its outer shape is adjusted to the attachment device in accordance with the inventions. The necessary requirements are given hereinafter. Measurement devices for the determination of the various properties are known. They include, for example, determination of structural properties such as the inner structure of tissue, but also the properties regarding the contents, e.g. the presence and concentration of certain substances in the living organism. Particularly preferred measurement devices are those for measuring analytes in blood, particularly preferred for measuring glucose. Tissue parts are in particular compartments of the organism that are found within a few centimeters, particularly within about 2 cm measured from the surface of the living organism. They include blood vessels. A particularly preferred optoelectronic measuring device is the one described in WO 91/10901.

BRIEF DESCRIPTION OF THE DRAWINGS

For a more complete understanding of the subject matter of the invention, reference should be made to the appended drawings, wherein.

DETAILED DESCRIPTION OF THE PREFERRED EMBODIMENTS

Figure 1A:
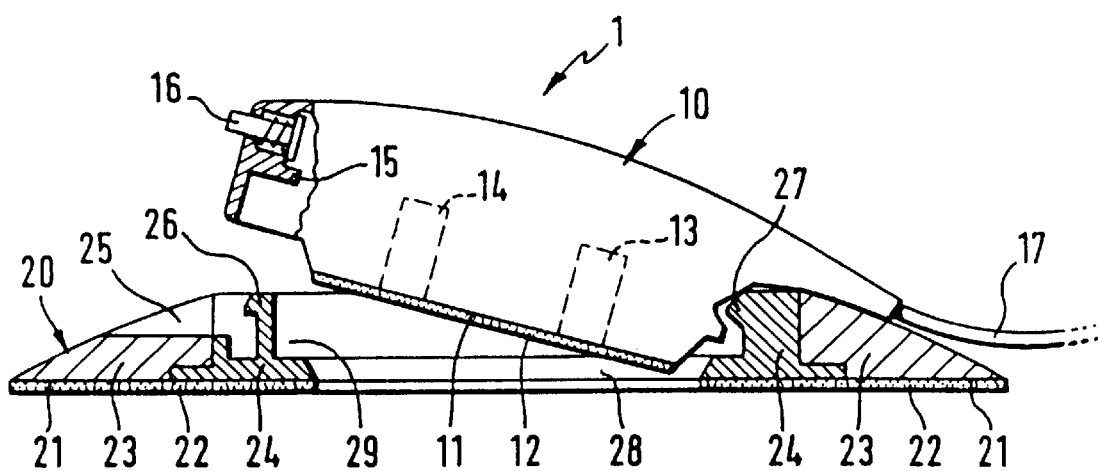
FIG. 1A is a cross-section view of an embodiment of the present invention.

In the following description, the first surface of the tissue resting on a first surface (11) of the measurement device (10) is referred to as first surface. The second tissue surface is the one that is laterally adjacent where a (second) surface (21) of the attachment device (20) can be placed so as to be directed toward the tissue.

The optoelectronic measuring device preferably has a first flat surface (11) which can be directed onto the first surface of the tissue. The first surface can be flat but also adjusted to the anatomy of the respective surface (body contours). This surface (11) contains at least one light emitter and at least one light receiver that are arranged such that the light emitted by the sender and scattered by the tissue can be detected by the receiver. The invention refers in particular to measuring arrangements where the site of detection is located on the same interface as the of incidence (i.e. measuring the reflectance as opposed to measuring the transmission where the site of incidence and the site of detection are located on opposite interfaces of the tissue).

An essential component of the system of the invention is a device (20) for attaching the measuring device (10) to the surface of the tissue from where it can be removed again without causing any damage. To ensure reliable positioning of the measuring device, the attachment device has components whose shape is made to match components of the measuring device. As understood in the invention, all those component pairs are suitable which allow reproducible removal and attachment of a sample with a high degree of positioning accuracy. The term reproducible is understood to be in such a manner that the measuring device can be removed and relocated several times without directing light receiver and light sender to different areas of the measuring window. Examples for such components are bayonet catches, screwed connections with abutments or catches, or clamping connections, and principally all types of flange systems (even those based on pressure). Particularly preferred are, however, components that do not require a rotational movement. Experience has shown that rotation of the measurement device causes the skin, against which the flat surface of the measurement device rests, to be moved. This moving of the skin reduces the reproducibility of the attachment of the measurement device with respect to the skin. It is, hence, preferred to use components that allow the measurement device to be inserted in the attachment arrangement in a direction that is perpendicular to the surface of the skin. It is particularly preferred to use components that provide an optical or acoustical control to monitor correct positioning. So-called snap closures are usually suitable for this purpose. Usually, it is necessary to provide two or several snap closures of which one can also be used as a guiding aid, e.g. a point of rotation or hinge. It has proven to be particularly favorable to use snap closures which can be opened by applying a slight lateral pressure which is not directed toward the tissue at the component linked to the measuring device.

The attachment device preferably contains a soft and a rigid material. The component linked to the attachment device is preferably connected to the rigid material of the attachment device. In a particularly preferred manner said component is made of a material which can endure numerous opening and closing procedures without negatively affecting the proper function. It can, but must not necessarily, be made of the same material as the rest of the attachment device. It can be a hook, for example. The component linked to the measuring device can be provided with a spring. This can be a hook which engages, as a consequence of the spring action, the hook provided at the attachment device. In another embodiment, a simple clamping closure is provided without spring action. Owing to the shape in accordance with the invention, the measurement device can only be fixed in its position in a predetermined and unique direction in the attachment device.

Both the soft and the rigid material surround the measurement window through which the non-invasive determination is accomplished. In a preferred embodiment, the attachment device is, hence, made of an inner component which is essentially annular and relatively small as compared to the extension of the surface of the tissue; it also has an edge made of a soft material which is relatively large as compared to the inner component. The result is an essentially annular attachment device with an inner and an outer diameter. Said diameter is, at its inner part, configured such that the optoelectronic measuring device can be linked to the ring or removed from it in an easy and reproducible manner, while it is robust (especially with respect to body movements) and fixed in its position. The inner ring is preferably made of a hard plastic, e.g. Delrin®. The outer large edge is made of a soft material, e.g. a material with a silicon-like softness; a thermoplastic material such as polyurethane is particularly preferred as that it can adjust to the form of the second surface of the tissue.

The inner and outer materials of the attachment device are linked to one another such that they do not come loose or twisted during regular use, i.e. while carrying the measurement device in the attachment device and while putting it on or taking it off. The rigid material is preferably incorporated in the soft material in such a manner that it is visible only at the sites where contact is made with the measurement device. The soft material essentially covers the entire surface of the attachment device provided to link the attachment device on to the tissue surface.

In addition to its attachment function, the attachment device also serves the purpose of protecting the first tissue surface from undesired light of the environment. The materials used for said device are, therefore, opaque to light, especially light that is used to determine the properties. This can be accomplished, for example, by pigmentation of the materials with light-absorbing substances.

A measuring window is a site at the attachment device through which the first surface of the organism is exposed to light from the measurement device and through which light scattered by the tissue arrives at the measurement device. It is, hence, a fundamental condition that the measurement window be transparent to incoming and scattered light. In a particularly simple and, hence, preferred embodiment, the measurement window is an opening in the material of the attachment device so that the flat surface of the measurement device can be brought into direct contact with the surface of the tissue when the measurement device is fixed in the attachment device.

It is also possible to provide several adjacent measurement windows, e.g. one window for each light emitter and each light receiver.

The attachment device is linked to its surface (21) on the second surface of the tissue preferably with the aid of a first adhesive. Experience has shown it to be particularly advantageous to use a double-sided adhesive tape. Such adhesive tapes are commonly known. The double-sided polyester adhesive tape manufactured by Adhesives Research (Art. No. AR 8254) based on acrylic glue is suitable.

Particularly suitable are adhesive tapes that allow fixation of the attachment device on the tissue, e.g. of human skin, over a period of several, preferably 3 days. It is preferred to have an adhesive that is moisture-absorbing. During this period, moisture (e.g. sweat) usually will be produced and remains on the skin due to a lack of aeration. This could lead to skin irritations. In another embodiment the adhesive used may be permeable to moisture. In this case it is expedient that the soft part of the attachment device be also permeable to moisture. This can be achieved by using perforated materials. The adhesive should not contain substances that may cause allergies.

Moreover, it is also preferred that the adhesive used can be more easily removed from the surface of the tissue after wearing than from the surface used for fixing it to the attachment device. This is possible with the adhesive given in the above example.

The adhesive used to link the attachment device to the tissue surface should also exhibit light absorbing properties. Advantageously, the invention avoids that light from the environment arrives at skin areas that are directly adjacent to the attachment device. Any arriving light can cause interfering signals at the light receivers after entering the tissue and penetrating the skin. It is particularly preferred that the outer diameter of the adhesive tape be slightly larger than the diameter of the attachment device. The areas of the adhesive tape which are not covered by the attachment device are preferably covered with a protective film that is opaque to light or are impregnated with a dye that is opaque to light in order to prevent external light from entering the measurement area or to reduce this effect as far as possible.

In a particularly preferred embodiment, the system of the invention has another (second) adhesive, i.e. in the form of double-sided adhesive tape, which is provided at the flat surface of the measuring device. Once the measurement device is placed in the attachment device, the adhesive acts as the actual interface between the surface and the measurement device. Since the light emitted from the measurement device and the light scattered by the tissue must pass through the adhesive, the material must have a high transmission for the wavelengths used. It should be as transparent as possible. Moreover, experience has shown it to be expedient if the adhesive does not have any light-guiding properties. This means, the adhesive should be selected such that it exhibits none or only very little reflection at its inner surfaces. A lateral transport of light caused by reflection at the inner surfaces or by inhomogeneities in the adhesive should be avoided in order to prevent cross talk between emitter and receiver by the adhesive. The adhesive is selected such that the loss of light is as small as possible when light is vertically travelling through.

Moreover, another reason why it is practically advantageous to have a tight connection between the first surface of the measuring device and the first surface of tissue is to have a close contact between the surfaces. The adhesive (12) ensures that a uniform distance be maintained between the tissue compartments and the measuring device. Moreover, a horizontal movement of the tissue surface relative to the measuring device, e.g. during movement, is largely reduced. Another advantage of the adhesive is that the surface of the tissue remains even. Spaces of air of different size between skin and measurement device, e.g. when goose-pimples are present, are thus avoided. The above listed complications of non-invasive determinations of properties on a living organism have so far been avoided in that some of the devices used for the measurement were pressed on to the surface with considerable pressure. The application of pressure on to the skin, however, alters tissue properties, e.g. blood flow, which in turn renders the devices unfit for long-term use. Owing to the fact that the device of the invention does not require pressure when adhesives are used (except when putting the device on) makes long-term application possible for the organism.

When this adhesive (12) is used, it is preferred that it have moisture-absorbing properties which have little to no effect on the optical properties. Thus it is possible to wear the measuring device for a period of 4 hours or more without interruption.

The adhesive force of the second adhesive (12) should be considerably lower than the one of the first adhesive (22). While the first adhesive has to supply practically the entire force to attach the system to the tissue, the adhesive properties of the second adhesive are of only minor importance. It should supply as much adhesive force as is necessary to maintain good contact between tissue and measuring device and to ensure that movement of the surface with respect to the measuring device is avoided. Moreover, it is preferred to have a lower adhesive force as compared to the first adhesive since it should be possible to remove the measuring device from the attachment device and the surface of the tissue without removing the attachment device from the surface. Suitable adhesives are acrylic adhesives. An example is the clear polyurethane adhesive tape manufactured by Adhesives Research (Art. No. AR 8133) which is based on the Hydro absorbent™ adhesive system with moisture absorbing and moisture permeable properties. This adhesive tape is a one-sided adhesive tape, but can also be provided as a double-sided tape by Adhesives Research upon request. Moreover, it is part of the technical knowledge of the expert to convert this adhesive tape into a double-sided adhesive tape. Moreover, it is preferred that the second adhesive can be more easily removed from the skin than from the surface of the measuring device.

Another adhesive that has proven well for both the attachment of the attachment device and of the measuring device on skin is manufactured by Lohmann and known as "Duplomed 2806". This adhesive and/or double-sided adhesive tape is both moisture absorbing and moisture permeable. It has sufficient light transmission perpendicular to the plane of the adhesive tape so that emitted light and scattered light from the radiated tissue parts can pass through. It has a sufficiently low light transport laterally, i.e. in the layer of the adhesive tape to avoid cross talk between light source and receiver. An adhesive tape with an even more effective suppression of cross talk can be obtained by dyeing with pigments, if this tape should work as a tape for attaching the attachment device.

Advantage of the present invention is the option of positioning the measuring device in an exact manner relative to the surface of the tissue. This includes both accuracy in vertical as well as in horizontal direction. The accuracy can be better than ±0.2 mm, preferably ±0.1 mm. It is also possible to achieve an improvement of the positioning accuracy with respect to a rotational axis perpendicular to the surface. A positioning accuracy is of particular importance as experience showed that, owing to the inhomogeneity of tissue, the reproducibility can be significantly improved with an exact and reproducible positioning of the measuring device. This also significantly reduces the number of recalibrations of the measuring device.

Moreover, it is possible in accordance with the invention to effectively prevent the incidence of light between the attachment device and the measuring device while the latter can still be easily removed.

In a preferred embodiment the outer form of the system which is not directed toward the tissue is configured such that it has as few corners and edges as possible. A flat structure is, hence, particularly preferred.

The measuring device itself must not contain all components that are necessary to carry out the determination. It is even preferred that some of the larger components (e.g. for evaluating the measurement) are provided in devices that are hooked up to the measurement device (10) via a connecting cable (17).

Another subject matter of the invention is a device for attaching an optoelectronic measuring device to the surface of a tissue of a living organism which comprises an annular shaped attachmend device (20) which surrounds a measuring window (28) and has at least one component (26) for the reproducible attachment of the measuring device.

In a preferred manner the attachment device of the invention has, on a flat surface, an adhesive for attaching the device to a surface of the tissue. The adhesive preferably exhibits light absorbing and/or moisture absorbing and/or moisture vapour permeable properties. The soft and the rigid materials preferably have light-absorbing properties. Moreover, the soft material also exhibits moisture absorbing and/or moisture-permeable properties. Additionally preferred embodiments for the system in accordance with the invention are described.

Another subject matter of the invention is a method for the preferably non-invasive determination of the properties of tissue parts of a living organism by means of
a) Attaching a device (20) that is opaque to light and surrounds a measuring window (28) and has at least one component (26) for reproducibly attaching the measuring device (10) to the surface of tissue.
b) Attaching the measuring device (10) to the device (20) so that device (10), through measuring window (28), is directed toward the surface of the tissue.
c) Exposing the tissue to light emitted by the measurement device.
d) Detecting the light scattered by the tissue in order to obtain a measurement value.
e) Repeating steps c) to d) during a period of at least 4 hours.

Preferred embodiments are indicated through the use of the system of the invention.

This method is made possible in that the measurement device remains attached over longer periods of time at one site on the surface of tissue. Owing to the use of an adhesive in accordance with the invention, there are no skin irritations.

Owing to the fact that attachment device can remain at the surface of the tissue when the measuring device is removed, it is possible to position the measurement arrangement on exactly the same site on the surface, e.g. after events that possibly may interfere with the measurement (e.g. showering).

It is preferred that the measurement device be removed from the (first) surface of the tissue such that the (second) adhesive remains at the measurement device when the latter is removed from the attachment device. Subsequently, the adhesive can also be removed from the measurement device and a new adhesive strip is attached to its surface when the device is again used. As is conventionally done when handling double-sided adhesive tape, the surface of the measurement device which is attached to the tissue surface is covered by an easily removable protective liner during transport or storage. This liner is removed immediately before the device is attached.

The attachment device remains on the surface of the tissue for a continuous period of time of several, preferably at least 3 days. If another determination interval is to be carried out, a new attachment device can be placed at the same site. When a new measurement is to be carried out at essentially the same site on the tissue, the position of the device to be removed can be marked on the tissue surface, e.g. at the edge of the measuring window. When a new attachment device is placed on the tissue it can be adjusted to match these marks.

When the measurement device is not attached in the attachment device, the opening (29) of the attachment device can be closed with the aid of a dummy which essentially matches the outer form of the measurement device, and therefore acts as a closure. It is thus possible to protect the measuring window, the snap mechanism and the first surface of the tissue from damaging influences (contamination, etc.) during a period when the measurement device is not worn.

Figure 1B:
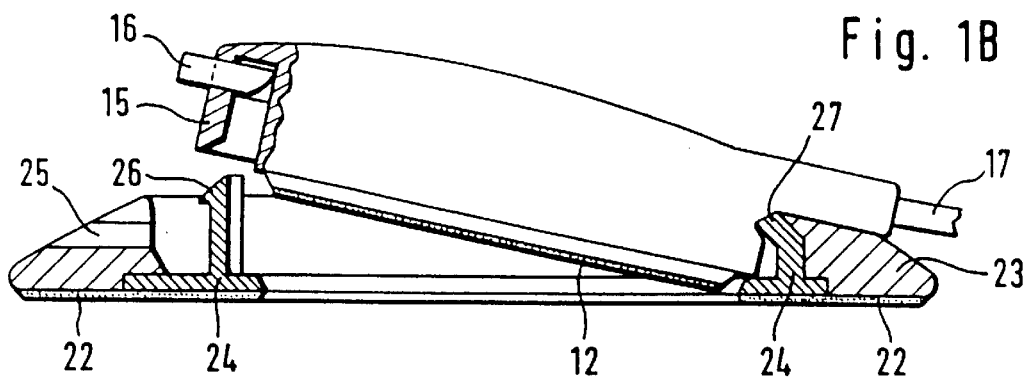
FIG. 1B illustrates another embodiment of the present invention.
Figure 1C:
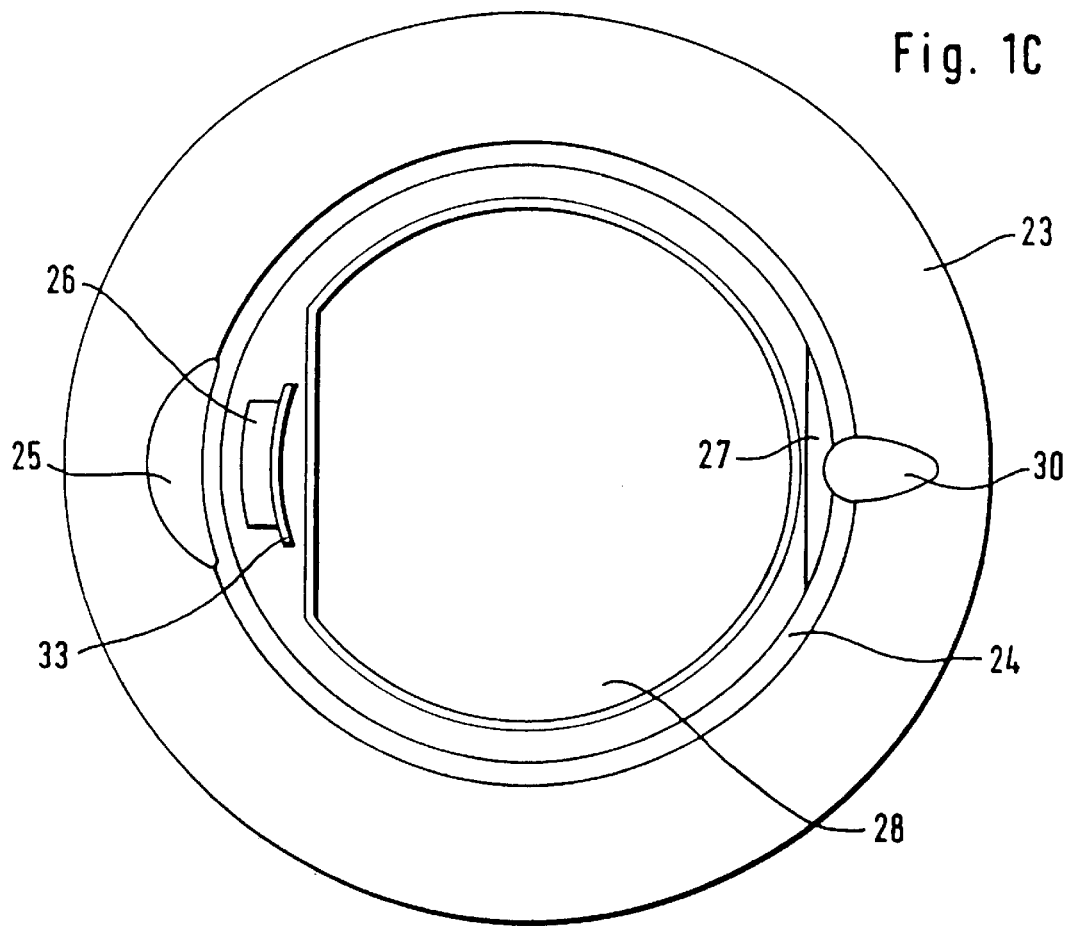
FIG. 1C discloses a top view of the attachment device of the present invention.

FIGS. 1A and 1B show a system where the measuring device is fixed in the attachment device with the aid of snap closure and a guiding aid that is located on the opposite site.

FIG. 1A shows a cross-section of the system when the opening of the measurement device already engages a guiding aid (27) of attachment device, while the snap connection on the opposite side has not yet engaged. The spring-mounted snap closure (15) of the measuring device can be opened with the aid of a press-button (16).

In FIG. 1B, the snap closure (15) of the measuring device is configured as a part of the housing and the connection can be released with the aid of simple, clamped press-button (16) without spring action. To do this, the measuring and attachment devices are released by applying lateral pressure on the projecting connecting piece (32) of press-button (16). The two bars (31) press against the projections (33) of the snap closure (26) of the attachment device. The hook connection of closure (26) and closure (15) are thus released.

Connection of the attachment device on the measuring device is achieved in that first the measuring device (10) is placed in the guide aid (27) at the attachment device. Subsequently, the connection between measuring and attachment device is achieved by applying slight pressure from top on the measuring device. Snap closure (15) of the measuring device will snap in below the snap closure (26) of the attachment device. Press-button (16) of FIG. 1B is automatically moved into its initial position.

Figure 1D:
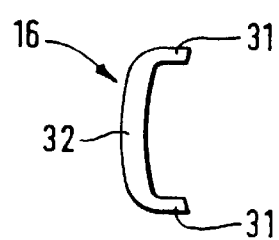
FIG. 1D is a top view of a clamping connection of the present invention.

In the embodiment of FIG. 1A, press-button (16) maintains an initial position due to the spring action exerted. FIG. 1D illustrates a top view of cramping connection (16) without the spring, comprising two bars (31) and larger, arch-like connecting piece (32).

Figure 2:
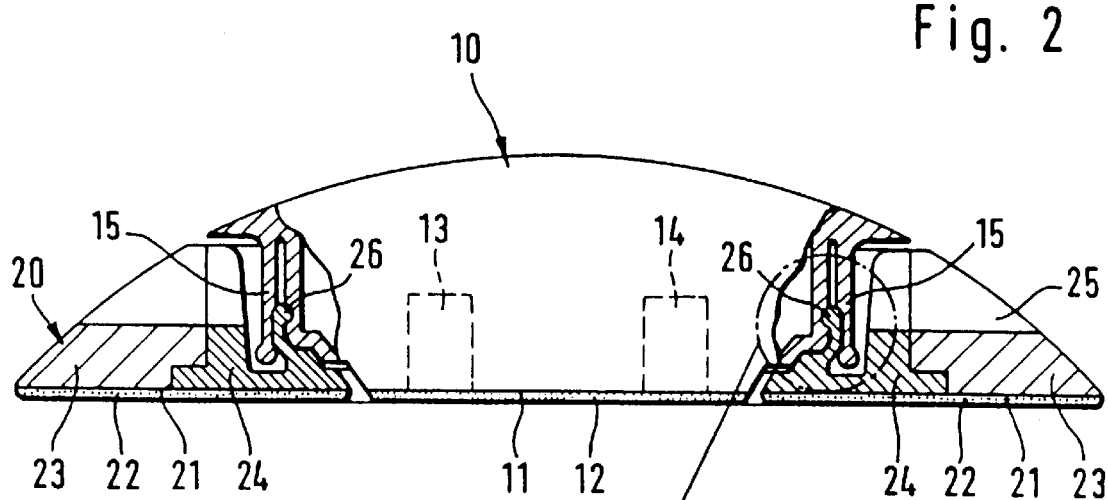
FIG. 2 discloses another embodiment of the present invention.
Figure 2A:
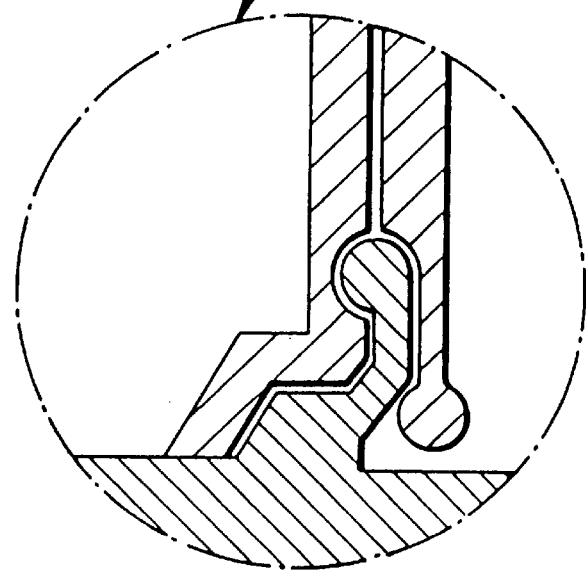

FIG. 2 shows an embodiment where the measurement device is fixed in the attachment device with the aid of an annular outer edge which engages a link located below the measurement device and snaps into a opening when a perfect fit is established. The drawing given in the circle gives details on component (26).

Although the present invention has been described and illustrated in detail, it should be clearly understood that the above descriptions are submitted for illustration and example only, and should not be taken as any type of limitation. The spirit and scope of the present invention is limited by the terms of the appended claims.

LIST REFERENCE NUMERALS (1) system
(10) measurement device
(11) surface of measurement device (first surface)
(12) adhesive on first surface of (10)
(13) light emitter (source)
(14) light receiver (detector)
(15) snap closure of measurement device
(16) press button
(17) connecting cable to evaluation unit
(20) attachment device
(21) surface of attachment device (second surface)
(22) adhesive on surface of (21)
(23) soft material
(24) rigid material
(25) recess to press button 16
(26) snap closure of attachment device (component)
(27) projection, guiding aid
(28) measuring window
(29) opening in the attachment device for measuring device
(30) recess for connecting cable
(31) bars
(32) connecting piece
(33) projections It is claimed:

1. A method for determination of properties of a biological matrix, said method comprising steps of:

providing an optoelectronic measurement means for performing optoelectronic measurements of the biological matrix;

providing a receiving means for removeably receiving the optoelectronic measurement means therein, said receiving means comprising a receiving housing for receiving the optoelectronic measurement means, and a measurement window allowing the optoelectronic measurement means to access the biological matrix;

attaching the receiving means to a first surface of the biological matrix, whereby the measurement window defines a second surface of the biological matrix;

attaching the optoelectronic measurement means to the receiving means said attaching including the steps of first engaging corresponding engaging elements on a first side of the optoelectronic measurement means and a corresponding first side of the receiving means in a tilted manner, then secondly engaging corresponding second engagement elements on a second side of the optoelectronic measurement means and a corresponding second side of the receiving means, thereby cooperatively engaging the optoelectronic measurement means and the receiving means, whereby the optoelectronic measurement means accesses the second surface of the biological matrix through the measuring window;

emitting light from the measuring device toward the second surface of the biological matrix;

detecting light scattered by the biological matrix with the optoelectronic measuring means;

determining a measuring value based upon the detected light;

re-emitting light from the measuring device, re-detecting light scattered by the biological matrix, and re-determining a measurement value, within four hours of the emitting, detecting and determining steps.

2. A method according to claim 1, comprising a step of, after the emitting, detecting, and determining steps, removing the optoelectronic measuring means from the receiving means, while the receiving means remains attached to the first surface of the biological matrix.

3. A method according to claim 2, further comprising a step of re-attaching the optoelectronic measurement means to the receiving means, then performing the steps of re-emitting, re-detecting, and re-determining.

4. A method according to claim 2, wherein the step of attaching the optoelectronic measurement means to the second surface of the biological matrix includes a step of adhering a surface of the optoelectronic measurement device to the second surface of the biological matrix with an adhesive.

5. A method according to claim 4, wherein said step of removing the optoelectronic measurement means from the receiver means also removes the adhesive from the second surface of the biological matrix.

6. A system for determining properties of a biological matrix, said system comprising:

an optoelectronic measurement means for performing optoelectronic measurements of a biological matrix, said optoelectronic measurement means comprising a first engagement element on a first side thereof, and a second engagement element on a second side thereof;

receiving means for removably receiving the optoelectronic measurement means, said receiving means comprising a receiving housing for receiving the optoelectronic measurement means therein, and a measurement window allowing the optoelectronic measurement means to access a first surface of the biological matrix, said receiving means including a third engagement element corresponding to the first engagement element of the optoelectronic measurement means, and a fourth engagement element corresponding to the second engagement element of the optoelectronic measurement means, wherein said receiving means and said optoelectronic measurement means are configured to be tiltingly engaged whereby said first engagement element and said third engagement element are engaged with each other, and said second engagement element and said fourth engagement element are then contacted to each other, thereby ensuring secure engagement between the optoelectronic measurement means and the receiving means.

7. A system according to claim 6, wherein said receiving means includes attaching means on a surface thereof, for attaching the receiving means to a second surface of the biological matrix whereby the optoelectronic measurement means can access the first surface of the biological matrix.

8. A system according to claim 7, wherein said attaching means comprises an adhesive.

9. A system according to claim 7, wherein said attaching means comprises a moisture permeable adhesive.

10. A system according to claim 7, wherein said attaching means comprises a moisture absorbing adhesive.

11. A system according to claim 7, wherein the attaching means comprises an adhesive having light absorbing properties.

12. A system according to claim 6, wherein said receiving housing is an annular housing surrounding the measurement window.

13. A system according to claim 7, wherein said attaching means comprises a double-sided adhesive tape.

14. A system according to claim 6, further comprising a measurement adhesive disposed on a measuring surface of the optoelectronic measurement means for attaching the measuring surface of the optoelectronic measurement means to the first surface of the biological matrix.

15. A system according to claim 14, wherein said optoelectronic measurement means includes a light emitting means which emits light of predetermined wavelength, and wherein said measurement adhesive is transparent to the predetermined wavelength.

16. A system according to claim 14, wherein said measurement adhesive has insignificant light guiding properties.

17. A system according to claim 14, wherein said measurement adhesive has moisture absorbing properties.

18. A system according to claim 6, wherein said optoelectronic measurement means comprises means for performing non-invasive determination of the properties of the biological matrix.

19. A system according to claim 6, wherein said receiving means comprises a base material of a first rigidity providing a stable substrate, and a soft material of a second rigidity on said base material, said second rigidity being softer than the first rigidity.

20. A system according to claim 6, wherein a surface of the optoelectronic measurement means which accesses the first surface of the biological matrix is a flat surface.

21. A system for determining properties of a biological matrix, said system comprising:

an optoelectronic measurement means for performing optoelectronic measurements of a biological matrix, said optoelectronic measurement means comprising a first engagement element on a first side thereof, and a second engagement element on a second side thereof;

receiving means for removably receiving the optoelectronic measurement means, said receiving means comprising a receiving house for receiving the optoelectronic measurement means therein, and a measurement window allowing the optoelectronic measurement means to access a first surface of the biological maxtix, said receiving means including a third engagement element corresponding to the first engagement element of the optoelectronic measurement means, and a fourth engagement element corresponding to the second engagement element of the optoelectronic measurement means;

a measurement adhesive disposed on a measuring surface of the optoelectronic measurement means to the first surface of the biological matrix;

wherein said receiving means and said optoelectronic measurement means are configured to be tilting, engaged whereby said first engagement element and said third engagement element are engaged with each other, and said second engagement element and said fourth engagement element are then contacted to each other, thereby ensuring secure engagement between the optoelectronic measurement means and the receiving means.

22. The system according to claim 2, wherein said optoelectronic measurement means includes a light emitting means which emits light of predetermined wavelength, and wherein said measurement adhesive is transparent to the predetermined wavelength.

23. The system according to claim 2, wherein said measurement adhesive has insignificant light guiding properties.

24. The system according to claim 2, wherein said measurement adhesive has moisture absorbing properties.

* * * * *